United States Patent [19]

Bourguignon et al.

[11] Patent Number: 5,648,659

[45] Date of Patent: Jul. 15, 1997

[54] METHOD FOR THE ACQUISITION, IN NUCLEAR MEDICINE, OF A SCATTER IMAGE

[75] Inventors: Michel Bourguignon, Sceaux; Christian Pare, Plaisir, both of France

[73] Assignee: Sopha Medical, Buc Cedex, France

[21] Appl. No.: 461,620

[22] Filed: Jun. 5, 1995

[30] Foreign Application Priority Data

Jun. 15, 1994 [FR] France .................................. 94 07332

[51] Int. Cl.⁶ .................................................. G01T 1/166
[52] U.S. Cl. .................. 250/363.04; 250/363.07
[58] Field of Search ..................... 250/363.04, 363.07

[56] References Cited

U.S. PATENT DOCUMENTS

| | | | |
|---|---|---|---|
| 4,982,416 | 1/1991 | Pare et al. ................... | 378/20 |
| 5,077,479 | 12/1991 | de la Barre et al. ............ | 250/363.1 |
| 5,105,086 | 4/1992 | Pierfitte et al. ................. | 250/363.08 |
| 5,155,756 | 10/1992 | Pare et al. ...................... | 378/196 |
| 5,214,287 | 5/1993 | Pare et al. ...................... | 250/363.1 |
| 5,359,198 | 10/1994 | Bourguignon et al. ......... | 250/363.07 |
| 5,390,225 | 2/1995 | Hawman ........................ | 250/363.04 |

FOREIGN PATENT DOCUMENTS

| | | |
|---|---|---|
| 106267 | 4/1984 | European Pat. Off. . |
| 9006083 | 6/1990 | WIPO . |
| 9102265 | 2/1991 | WIPO . |
| 9311705 | 6/1993 | WIPO . |

OTHER PUBLICATIONS

*IEEE Transactions on Medical Imaging*, vol. 13, No. 2, Cree et al, "Towards Direct Reconstruction from a Gamma Camera Based on Compton Scattering," pp. 398–407, Jun. 1994.

*The Journal of Nuclear Medicine*, vol. 29, No. 2, Macey et al, "Comparison of the Three Boundary Detection Methods for SPECT Using Compton Scattered Photons," pp. 203–207, Feb. 1988.

*Primary Examiner*—Carolyn E. Fields
*Attorney, Agent, or Firm*—Kerkam, Stowell, Kondracki & Clarke; Dennis P. Clarke

[57] ABSTRACT

To acquire both a scatter image and an emission image in nuclear medicine, it is chosen to detect the emission image by validating the radioactive events that occur in the nominal range of the radioactive marker chosen. For the scatter image, lower energy ranges are chosen, these ranges corresponding to the production of at least secondary or tertiary Compton photons. It is shown that it is possible, in this way, to reconstruct an artifact-free transmission image. This scatter image is used to correct the initially acquired emission image. It is shown that it is possible to acquire both images at the same time.

22 Claims, 2 Drawing Sheets

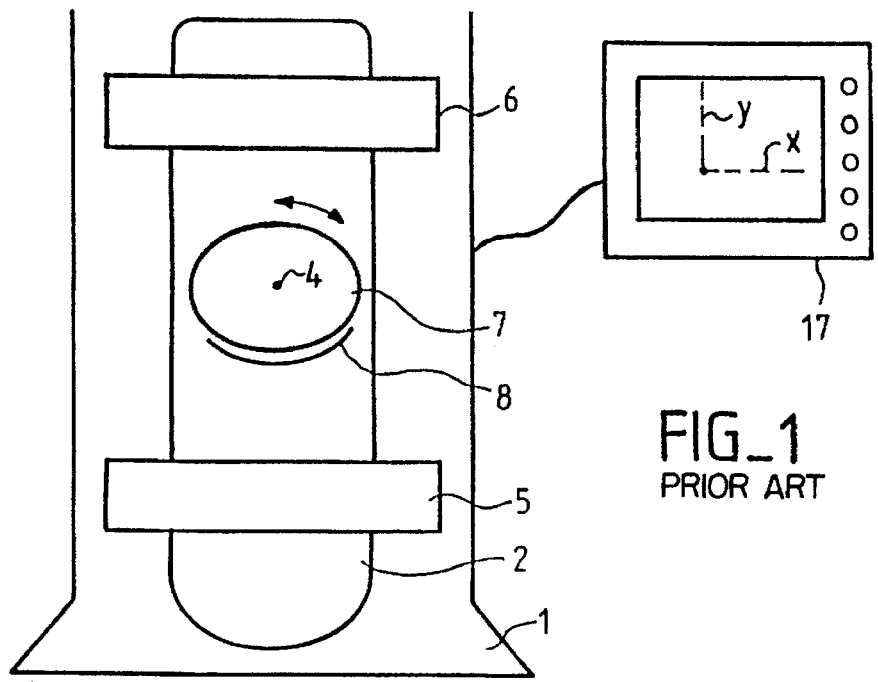
FIG_1
PRIOR ART
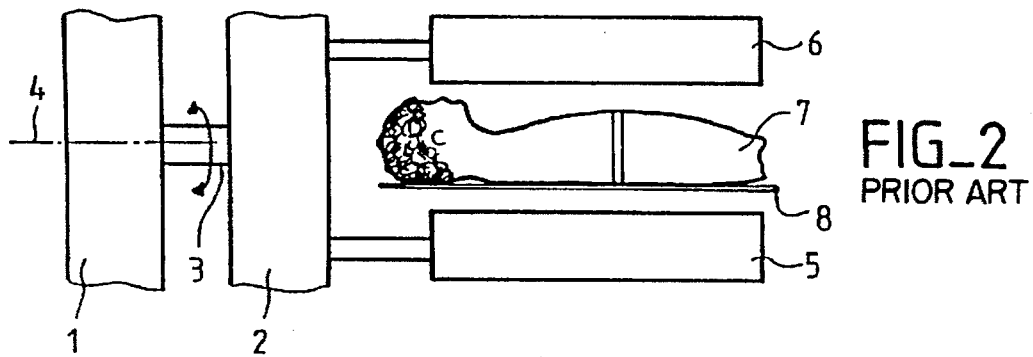
FIG_2
PRIOR ART
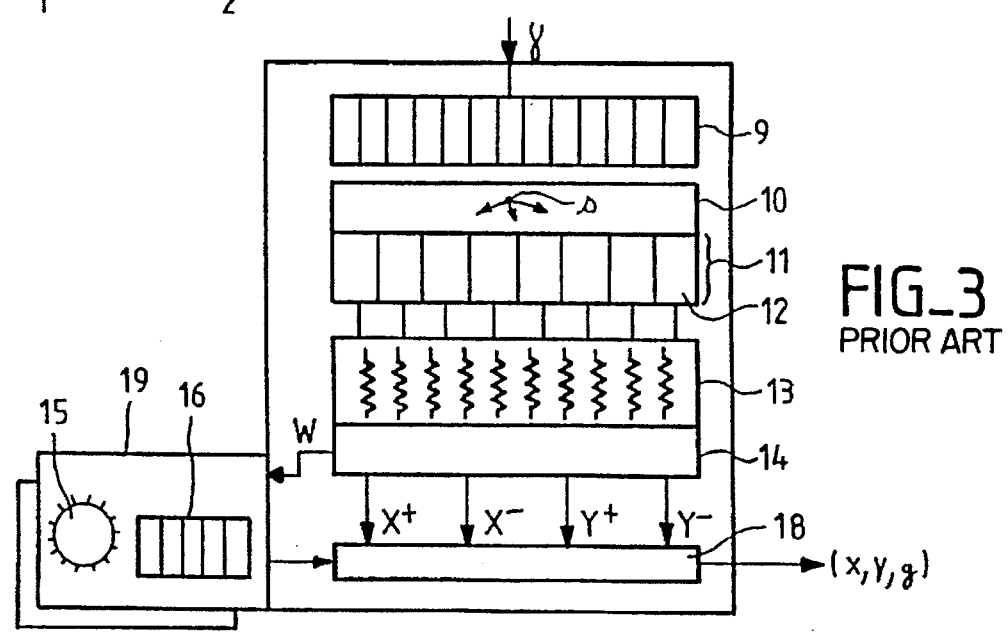
FIG_3
PRIOR ART

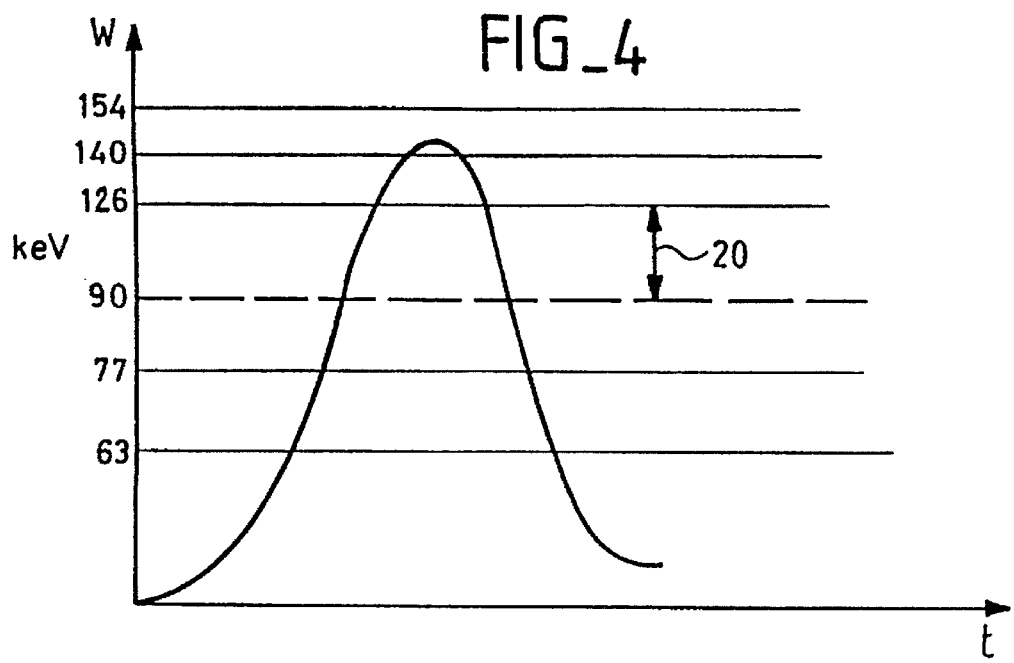
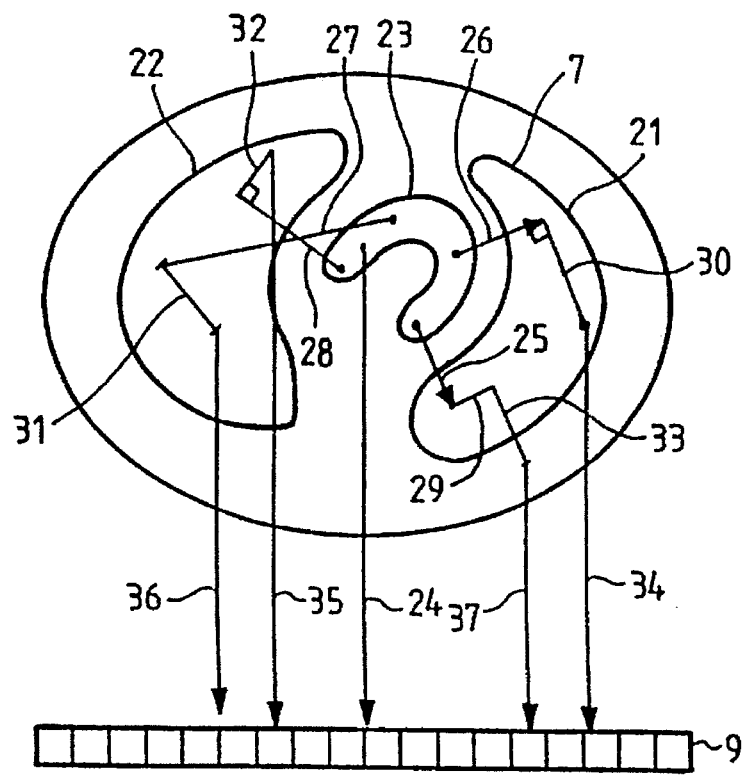

METHOD FOR THE ACQUISITION, IN NUCLEAR MEDICINE, OF A SCATTER IMAGE

BACKGROUND OF THE INVENTION

1. Field of the Invention

An object of the present invention is a method for the acquisition, in nuclear medicine, of a scatter image (i.e. an image obtained by scatter as defined here below) of the body of a patient being examined. The scatter image thus obtained may be used as such to reveal the anatomy of the examined body. Preferably, it will be used to correct the results of an emission image (i.e. an image obtained by emission as defined here below) revealed by the same machine. The value of the invention is that, in the latter case, it is possible to acquire both images simultaneously. This results in a gain in time and above all in a far better geometrical comparison of the two images acquired to enable the correction of the results of one of them as a function of those of the other.

2. Description of the Prior Art

Nuclear medicine is a branch of diagnostic medicine in which it is sought to obtain functional information about the bodies of the patients examined. To this end, radioactive markers are injected in these patients. The marker used is generally technetium. This radioactive marker, depending on the biological agent that carries it, will get fixed into one organ or another of the patient. At the place where it is fixed, it sends out radioactive radiation, namely gamma rays. The greater the quantity of markers fixed in the organ, the greater is the number of these rays. This is a phenomenon of emission.

To measure this radioactive phenomenon, a gamma camera or scintillation camera is used. A nuclear medicine machine therefore essentially has a mount to support a gamma camera of this type. This camera has a detector and means to compute the detected image. The detector has a scintillator crystal. Generally, the scintillator crystal is plane. The scintillator absorbs the gamma radioactive radiation. By photo-electrical effect, it emits a luminous scintillation in response. This luminous scintillation is detected downline by an array of photomultiplier tubes of the detector. In addition, a gamma camera has a control and processing panel. The tubes are thus associated with computation means. These means make it possible to determine the coordinates of a locus of interaction of the gamma rays in the scintillator. This locus reveals the projected image of the body.

In view of the fact that the radioactive emission in the body is omnidirectional, this localizing can be carried out efficiently only by the interposing of a collimator between the body and the scintillator. This collimator lets through only the radioactive rays that get propagated in a chosen direction.

With such examinations by emission, it is possible to produce projection images. If the gamma camera is rotated about the patient's body while the radioactive phenomenon occurs (for an examination period of about half an hour), it is possible to acquire a certain number of projections, for example parallel-type projections. With these parallel-type projections it is possible, by means of tomography type methods, to reconstruct sectional images of the body. The projections are of a parallel type because the collimator lets through the rays in only one direction perpendicular to its plane.

However, the mode of acquisition thus briefly recalled has a drawback: the gamma rays emitted by the internal structures of the body must cross other regions of this body before exciting the scintillator and, in these other regions of the body, they undergo a corresponding attenuation. This attenuation disturbs the acquisition of the acquired images and the exactness and precision of the reconstructed images. Many attempts have been made to take account of this attenuation, sometimes without really measuring it. However, the method thus proposed has given few results and, to date, the real measurement of attenuation, notably by transmission tomography, is the only approach that can be envisaged. The knowledge obtained, by such a method, of the attenuation coefficient related to the radiological density at each position of the body makes it possible to correct the results of the images obtained by emission. The correction takes account of the varying size of the mass of the tissues interposed in the path of a radioactive emission coming from a disintegration of the marker.

French patent application No. 89 10225 filed on 28 Jul. 1989 and published under No. 2 650 397, recommends the performance of such a transmission-type measurement of the internal structures of the body with a device comprising an external point source of gamma radiation facing the detector of the gamma camera. The body is interposed between this source and this detector. In practice, it has been shown that moving this point source to a distance of about one meter from the face of the detector could suffice to obtain transmission images. The term "transmission image" herein means that the radiation measured is a radiation that goes through the body from one side to the other, the source of radiation being external: the body transmits (or does not transmit) the gamma radiation. For the reconstruction of tomographic images, in this patent application, it has been shown that it is enough to make a slight correction of the reconstruction algorithms to take account of the conical nature of the radiation.

However, this method has drawbacks. The first drawback is that the patient's body must be subjected to a first irradiation with this external source and that there is therefore a loss of time. The second drawback results from the conical nature of the radiation. Indeed, owing to the limited sizes of the detector, the patient's body cannot be entirely included in the radiation cone. Certain parts of the body, close to the generatrix lines of the cone, are not usefully subjected to the radiation except when these parts are as close as possible to the plane of the detector. For reasons of acquisition of a tomographic image, the gamma camera was rotated by a half-turn about the patient's body. These very same regions are then at the greatest distance from the plane of the detector and are either not irradiated or irradiated, the result of this radiation, however, going beyond the limits of the detector.

Consequently, the reconstruction of the images for these parts which are sometimes taken into account and sometimes not taken into account leads to the creation of artifacts. In practice, it is necessary, for the reconstruction, to limit the operation to the part that is seen whatever may be of the incidence of the gamma camera.

Furthermore, in an article by D. J. Macey et al., "Comparison Of Three Boundary Detection Methods For SPECT Using Compton Scattered Photons, " *Journal of Nuclear Medicine*, Vol. 29, No. 2, February 1988, a method has been devised for the acquisition of images by transmission by the use of the Compton effect. To this end, this article makes a comparison of the images obtained depending on whether the radioactive source is inside or outside the patient's body and, in the latter case, depending on whether the Compton photons have to be measured at 90° or at 180°. The radioactive marker used is technetium whose radiation energy is 140 KeV. In any case, a series of experiments are undertaken in making the body rotate before the detector of the gamma camera.

The conclusions of this article are that the results of the experiments with internal radioactive source are unusable, whereas they are acceptable when the source is external. In any case, what occurs is not a real transmission but a pseudo-transmission: quite simply, the radiation does not directly come from an injected organ. Hereinafter in the present explanation, the term "scatter" is used to distinguish this phenomenon from "emission" (which is related to the injection of the marker).

For the experiment in which the radioactive marker has been injected into the structure being examined, the energy window opened to measure the Compton photons was centered on 110 KeV and had a width of ±15%: from 94 to 127 KeV. In practice, given that for technetium at 140 Kev the lower limit of the energy of the Compton photons taken into account is 90 KeV (with backscattering at 180°), and given that, furthermore, for reasons of detection, it is accepted that a window of ±10% around 140 KeV (126 KeV–154 KeV) can be opened to measure the primary gamma radiation, it may be assumed that this experiment has taken account of all the possible Compton photons. Nevertheless, the conclusions drawn by the authors of the article are such that the reconstruction of the contours with an internal source is difficult and even that it is not efficient enough to carry out a quantitative appreciation.

The problem therefore is to be able to do without an external source whose handling is furthermore always dangerous for the handlers, this external source being the cause of loss of time and hence loss of the profitability of the machine.

The idea of the invention however is to use the gamma radiation source as injected into the patient to acquire a scatter image at the same time as the acquisition of the emission image due to the radioactive marker. To this end, in the invention, rather than opening an energy window tending to take account of the primary Compton photons which, in principle, are the most numerous, it has been chosen on the contrary to take account of the secondary Compton photons, or even the tertiary Compton photons, by lowering the energy window so that a substantial part of this window is located beyond the lower limit of emission of the primary Compton photons. For example, for primary Compton photons produced by technetium, this limit is 90 KeV.

In practice, it has been realized that firstly, by acting in this way, a sufficient amount of information is obtained to enable the production of the images and that, secondly, the images produced are not affected by artifacts. It is likely that, with the choice of the invention, the different parts of the body are taken into account more efficiently. This is because the secondary or tertiary Compton photons have locations of emission, locations at which the secondary or tertiary Compton events occur, that are better distributed within the body.

Various tests have been carried out and it has been observed that, provided that the range taken into account includes a substantial part located outside the range of primary radiation and the range of the primary Compton photons, it is possible to obtain a good image.

SUMMARY OF THE INVENTION

An object of the invention therefore is a method for the acquisition, in nuclear medicine, of a scatter image of a patient's body wherein said method comprises the following steps:

the patient's body is placed in a nuclear medicine machine, an irradiating marker emitting radioactive rays in a given energy range E is injected into the patient's body, a detection is carried out, with a detector of the machine, of the radiation that occurs within the patient's body and has an energy range of 0.75 E to 0.35 E.

According to one explanation of the invention, an irradiating marker is injected into the patient's body. This marker emits radioactive rays in a given energy range E. A detection is carried out, with the detector of the machine, of the radiation occurring within the patient's body, the energy of which essentially corresponds to that of the range of re-emission of at least secondary or tertiary Compton type photons, the upper limit of which is fixed by the re-emission at 180°.

According to another explanation of the invention, a detection is carried out, with the detector of the machine, of the radiation occurring inside the patient's body, the energy range of which is such that the locations of these phenomena of re-emission are statistically distributed in a substantially equal manner in all the locations.

BRIEF DESCRIPTION OF THE DRAWINGS

The invention will be understood more clearly from the following description and from the appended figures. These figures are given purely by way of an indication and in no way restrict the scope of the invention. Of these figures:

FIGS. 1 and 2 show front and sectional views of a nuclear medicine machine that can be used to implement the method of the invention;

FIG. 3 shows a schematic view of the working of a detector of a gamma camera;

FIG. 4 is an energy diagram of a radioactive event and the preferred energy ranges of the method of the invention;

FIG. 5 shows a schematic view of a secondary or tertiary Compton radiation.

MORE DETAILED DESCRIPTION

FIGS. 1 and 2 show a nuclear medicine machine, also called a gamma camera, that can be used to implement the method of the invention. FIG. 1 is a front view, FIG. 2 is a sectional view of FIG. 1 along a vertical plane perpendicular to this FIG. 1. The machine has a frame 1 holding a mount 2. The mount 2 is held on the frame 1 by a rotation shaft 3 capable of rotating in the direction of the arrows about an axis 4. The mount 2, in this example, holds two detectors 5 and 6 spread away from each other to receive, between them, the patient's body 7 lying on a bed 8. The machine could nevertheless have only one detector or more than two detectors. There are known machines thus having up to twenty detectors.

The principle of the acquisition of an image is as follows. For a given position in orientation of the detectors with respect to a body 7, the gamma rays coming from this body go through a collimator 9 (FIG. 3) placed on a face of the detector facing the body 7. The collimator 9 may have holes that are straight or oblique, and parallel or convergent. The presence of a collimator makes it possible to avoid taking account of a troublesome scattered radiation. After passing through the collimator, the gamma photons which are in the right direction of propagation cause a scintillation s in the scintillator crystal 10 placed on the other side of the collimator 9. The scintillation s produced by the scintillator 10 is detected by an array 11 of photo-multiplier tubes such as 12 that produce electrical signals corresponding to the scintillation that they have detected. These signals are transmitted to processing circuits comprising in particular a network 13 of barycenter-weighting resistors to weight the electrical signals produced by the different tubes in order to prepare electrical localization signals called X+, X−, Y+ and Y− representing a location in the scintillator 10 in which the measured scintillation is produced. To this end, the network of resistors 13 is linked to an amplification circuit 14 that prepares these electrical localization signals.

The circuit 14 also produces an energy signal W enabling, for each scintillation s, to know its total energy.

At the time of an experiment, the range of energy in which the machine is designed to work is adjusted by means of control buttons such as 15 and tuning indicators 16. In practice, the buttons 15 may quite simply be a keyboard of a control computer of the machine and the display unit 16 may be the screen 17 of this computer. Through this configuration, means are conventionally available, in any nuclear medicine machine, to indicate the range of energy to be taken into account. For example, for emission images with a technetium type radioactive marker emitting gamma photons at 140 KeV, it is conventional to center the energy window of reception on 140 KeV and to open it by ±10%, namely between 154 KeV and 126 KeV.

The device 19 for adjusting this energy range is coupled to a filtering circuit 18 that validates the taking into account, in the rest of the processing performed by the gamma camera, of the localizing signals if the energy of the gamma pulse measured is within the chosen range.

In the invention, the buttons 15 are used first of all to adjust the range so that it is located between 0.75 E and 0.35 E, E being the energy of the gamma rays normally emitted by the radioactive marker used. The adjusting of this range must, in practice, correspond essentially to the range of re-emission of at least secondary or tertiary Compton type photons. It is thought that by acting in this way, it is certain that an equal statistical distribution of the locations of re-emission will be obtained. Indeed, it may be estimated that the density of the re-emission of primary Compton photons decreases with distance from the source of gamma rays and with distance from the organ in the body that has been injected. By contrast, since these are secondary or primary rays, it would seem that their distribution is improved. In any case, this leads, as we have seen by experiment, to a better rendering of the images. In particular, the contours that do not appear in the article quoted are now clearly shown.

Each detector therefore has a circuit 18 downline with respect to the circuit 14. This circuit 18 has two tasks. Firstly, it produces electrical signals X and Y that provide information on the precise position, in the image produced of the location of the scintillation s (and hence correspondingly the image of the location, in projection, where the primary gamma emission or the primary, secondary, tertiary Compton radiation has occurred in the body 7). The detection of this event results in the revealing, on the display screen 17, of the images of a light dot at the position of the image that corresponds to these X, Y coordinates. However, it is also the case that this revelation occurs only if, furthermore, the measured energy W corresponds to the range adjusted with the buttons 15. If the measured energy corresponds to this range, the window selection circuit 19 delivers a signal that enables the working of the circuit 18. If not, it produces nothing: the radioactive event is ignored.

FIG. 4 shows an energy signal W developing as a function of time when a scintillation occurs. The period of the electrical pulse delivered by the tubes 12 for each scintillation is very short, in the range of some nanoseconds. During this period, the electrical signal rises and then falls and returns to zero. If the radiation is a primary gamma radiation due to technetium, this pulse must normally culminate in a value corresponding to 140 KeV. Thus, to reveal emission images (where the primary gamma radiation is taken into account), the detection window is set between 126 KeV and 154 KeV. The primary Compton radiation for one and the same marker produces gamma rays whose energy is not lower than 90 KeV. The part of the range of FIG. 4 marked by the double arrow 20 was the part of energy examined by the experiments that were described in the above-mentioned article and that led to the rejection of the technique.

In contrast to this negative teaching, the contribution of the invention is that, on the contrary, very good results are obtained once the detection window is centered beyond the low limit value of production of the primary Compton rays.

It may be observed that, with the invention, good results have been obtained with windows at ±15%, provided that the center of the window is placed below the minimum energy of the primary Compton rays. For example, for technetium, it may be chosen to have a window center of up to 90 KeV and hence a window open between 105 KeV and 75 KeV. Similarly, fairly low values have been tested, also giving good results. In practice, it has been determined that the energy range to be used must range from 0.75×E to 0.35×E, E being the energy of gamma radiation of the marker used.

The prior art gamma cameras are normally designed to enable the setting, with the device 19, of a window corresponding to technetium: 140 KeV. They are furthermore also designed to set the reception on an energy window corresponding to thallium: 70 KeV. In practice, in the invention, the protocol chosen to reveal the scatter image will be the thallium protocol whereas the marker injected into the body is technetium. This is because the acquisition protocols for thallium are normally preprogrammed in all the machines. As a result, no changes will have to be made in existing machines to make them reveal the scatter image acquired according to the method of the invention. All that needs to be done is to choose a range of energy as indicated here above.

However, when both images, namely the emission and scatter images, have to be acquired simultaneously, then it is chosen to duplicate the circuit 19. This may be done physically, and, in this case, the circuit 18 will also be duplicated. Or, preferably, a modification will be made in the processing program implemented by the image processing computer used by the machine. Conventionally, a nuclear medicine machine keeps an account, for a given duration, at each pixel of an image to be created, of the number of radioactive events that have been produced therein. The luminosity of the pixels depends on this number. This distribution of luminosity reveals the contours of the image of the body. Hence, normally, the image processing system of the machine has a computer program that increments the number of events assigned to a location X, Y in the image by one unit whenever it receives signals X, Y delivered by the circuit 18. In the invention, the signals delivered by the circuit 18 will either be duplicated because there are two circuits 18 or preferably complemented by an information element g pertaining to the range that shall be given by the circuit or circuits 19.

Thus, when a radioactive event occurs in the body and is detected by the scintillator, either this event corresponds to a primary radiation (140 KeV) and the counting of the event is assigned to the emission image (for example g=0), or the energy of this radioactive event has culminated in the selected range for the secondary or tertiary Compton events (70 KeV±10%=77 KeV–63 KeV) and the event is accounted for at the X, Y coordinates to contribute to the construction of the scatter image (and in this case g=1). Or again, the energy of the radioactive event culminates outside the selected ranges. In this case, it is quite simply eliminated and the electrical signals X and Y are sent to neither of the two images. At the end, the two images are obtained simultaneously.

FIG. 5 gives a schematic view of what happens within the body 7 of the patient throughout the period of the acquisition. This figure shows the lungs 21 and 22 as well as the heart 23 shown in a sectional view. Because of the biological agent used, it may be estimated that only the heart 23, at least initially, emits primary gamma radiation. Primary gamma rays 24 will thus strike the collimator 9. If these gamma rays are rightly oriented, they go through the collimator and are taken into account to reveal the presence of the heart in the emission image.

Among the gamma rays that are not taken into account for the emission image, there are gamma rays that undergo Compton scattering as shown at 25 to 28. At the position of the Compton impact, a primary Compton radiation, 29 to 32 respectively, is produced. These primary Compton photons themselves give rise to secondary Compton photons 33 to 36, some of which are detected by the detector 5 because they have the right orientation. These are the photons 34 to 36. Some of the photons are not detected either because they do not have the right orientation or because they themselves give rise to a tertiary Compton photon 37 which for its part will have the right orientation. It is likely that, with the choice of the invention using secondary or tertiary Compton rays, an improved distribution is obtained, in the body 7, of the locations at which these low energy level Compton photons arise. These locations are distributed more uniformly than could be the case with the primary Compton rays.

Thus, an astonishing result is obtained in the sense that, to reveal the operation of the heart, it has been possible to continue the concentration, with the biological agent chosen, of the presence of the radioactive marker in the heart while at the same time also obtaining an efficient distribution, throughout the patient's body, of the locations of emission of the secondary or tertiary Compton rays. It is not necessary in practice to inject the patient with a marker that would spread throughout this patient's body. Finally, one of the difficulties revealed in the above-mentioned article, which had been circumvented therein by the extraction of the radioactive source from the body, is now resolved by keeping the radioactive source within the body (in the heart), but obtaining a more efficient distribution of the locations of creation of the photons to be detected by choosing a lower range of energy.

For the correction of the emission image that is obtained simultaneously with the scatter image, it has been furthermore discovered that it is enough to be satisfied with a transmission image that is segmented and quantified on a limited number of segments. In the case of a binary segmentation for example, the tissues are thus considered to be dense or not dense depending on whether the number of strokes counted vertically to each place of the image is above or below a threshold. This "binarization" of the image can be done in two ways. According to one possibility, preferably, the scatter images are acquired for several directions of incidence of the detectors about the patient's body and, with these projection images at different directions of incidence, a scatter image is reconstructed as for a normal emission image. This scatter image is then made binary or tertiary or quaternary. The emission image is then corrected according to the known modes as a function of this binary image or pseudo-projection image deduced therefrom. It is also possible to perform a "binarization" of the transmission images in projection obtained for each of the angles of incidence before recomputing the tomography of the emission image for which all the projections will be corrected. For the correction, each segmented pixel is assigned an attenuation coefficient corresponding to the biological tissues identified. This correspondence is preferably an a priori correspondence. For example, it is 0.15 $cm^{-1}$ for the biological tissues, 0.18 $cm^{-1}$ for blood, 0.4 $cm^{-1}$ for the lungs.

The marker may be injected so that it is fixed in the heart. It is also possible to inject it in another form so that it is fixed in the liver, the lungs, etc. In any case, preferably a localized fixing will be chosen if it is desired to acquire both images at the same time.

What is claimed is:

1. A method for the acquisition, in nuclear medicine, of a scatter image of a patient's body wherein said method comprises the following steps:

the patient's body is placed in a nuclear medicine machine, an irradiating marker emitting radioactive rays in a given first energy range E is injected into the patient's body, a detection is carried out, with a detector of the machine, of the radiation emitted from within the patient's body by said marker and that has a second energy range of 0.75 E to 0.35 E, and a conversion of said detected radiation in said second energy range into said image.

2. A method according to claim 1, wherein a detection is carried out, with a detector of the machine, of the radiation that occurs within the patient's body and that has an energy range of 0.55 E to 0.45 E.

3. A method according to claim 1, wherein the scatter image is acquired at the same time as an emission image by the measurement, in the rays coming from the patient's body, of those rays ranging from 0.35 E to 0.75 E and by the separation of those rays which correspond to the energy E to produce the emission image of the rays corresponding to the range of scatter energy.

4. A method according to claim 1, wherein a marker containing technetium 99 m is injected and a detection is carried out, for the scatter image, of the radiation occurring in an energy range corresponding to thallium.

5. A method according to claim 1 wherein:

during the acquisition, the detector is made to occupy a plurality of positions about the patient's body, and a tomographic image of radiological density of the tissues within this body is deduced therefrom.

6. A method according to claim 5, wherein:

the tomographic image of radiological density is segmented by the attribution, to each pixel of this image, of the densities of a given type depending on whether the density measured for these pixels is within a range.

7. A method according to claim 1 wherein the emission image is corrected as a function of the results of the scatter image.

8. A method according to claim 1, wherein the radioactive marker is injected in such a way that it gets fixed in the patient's heart or lungs.

9. A method for the acquisition, in nuclear medicine, of a scatter image of a patient's body wherein said method comprises the following steps:

the patient's body is placed in a nuclear medicine machine, an irradiating marker emitting radioactive rays in a given energy range E is injected into the patient's body, a detection is carried out, with the detector of the machine, of the radiation emitted from within the patient's body by said marker, the energy of which essentially corresponds to that of the range of re-emission of at least secondary or tertiary Compton type photons, the upper limit of which is fixed by the re-emission at 180°, and a conversion of said detected radiation in said re-emission energy range into said image.

10. A method according to claim 9, wherein the scatter image is acquired at the same time as an emission image by the measurement, in the rays coming from the patient's body, of those rays ranging from 0.35 E to 0.75 E and by the separation of those rays which correspond to the energy E to produce the emission image of the rays corresponding to the range of scatter energy.

11. A method according to claim 9, wherein a marker containing technetium 99 m is injected and a detection is carried out, for the scatter image, of the radiation occurring in an energy range corresponding to thallium.

12. A method according to claim 9, wherein:

during the acquisition, the detector is made to occupy a plurality of positions about the patient's body, and a tomographic image of radiological density of the tissues within this body is deduced therefrom.

13. A method according to claim 12, wherein the tomographic image of radiological density is segmented by the attribution, to each pixel of this image, of the densities of a given type depending on whether the density measured for these pixels is within a range.

14. A method according to claim 9, wherein an emission image is corrected as a function of the results of the scatter image.

15. A method according to claim 9, wherein the radioactive marker is injected in such a way that it gets fixed in the patient's heart or lungs.

16. A method for the acquisition, in nuclear medicine, of a scatter image of a patient's body wherein said method comprises the following steps:

the patient's body is placed in a nuclear medicine machine, an irradiating marker emitting radioactive rays in a given first energy range E is injected into the patient's body, a detection is carried out, with the detector of the machine, of the radiation emitted from inside the patient's body by said marker at a second energy range, the second energy range being such that the locations of the phenomena of re-emission are statistically distributed in a substantially equal manner in all the locations, and a conversion of said detected radiation in said second energy range into said image.

17. A method according to claim 16, wherein the scatter image is acquired at the same time as an emission image by the measurement, in the rays coming from the patient's body, of those rays ranging from 0.35 E to 0.75 E and by the separation of those rays which correspond to the energy E to produce the emission image of the rays corresponding to the range of scatter energy.

18. A method according to claim 16, wherein a marker containing technetium 99 m is injected and a detection is carried out, for the scatter image, of the radiation occurring in an energy range corresponding to thallium.

19. A method according to claim 16, wherein:

during the acquisition, the detector is made to occupy a plurality of positions about the patient's body, and a tomographic image of radiological density of the tissues within this body is deduced therefrom.

20. A method according to claim 19, wherein the tomographic image of radiological density is segmented by the attribution, to each pixel of this image, of the densities of a given type depending on whether the density measured for these pixels is within a range.

21. A method according to claim 16, wherein an emission image is corrected as a function of the results of the scatter image.

22. A method according to claim 16, wherein the radioactive marker is injected in such a way that it gets fixed in the patient's heart or lungs.

* * * * *